United States Patent
Weiss

(10) Patent No.: US 6,243,486 B1
(45) Date of Patent: Jun. 5, 2001

(54) SYSTEM FOR COUNTING COLONIES OF MICRO-ORGANISMS IN PETRI DISHES AND OTHER CULTURE MEDIA

(76) Inventor: Marvin Weiss, 51 Turtle Bay Dr., Branford, CT (US) 06405

( * ) Notice: Subject to any disclaimer, the term of this patent is extended or adjusted under 35 U.S.C. 154(b) by 0 days.

(21) Appl. No.: 09/351,030

(22) Filed: Jul. 9, 1999

Related U.S. Application Data

(63) Continuation of application No. 08/708,018, filed on Aug. 30, 1996.

(51) Int. Cl.$^7$ ........................................................ G06K 9/00
(52) U.S. Cl. ............................................. 382/133; 435/39
(58) Field of Search ................................... 382/128–134, 382/162, 172, 256, 266, 274, 192, 100, 181, 194, 203, 260; 435/30–34, 39, 40.5, 41, 385; 429/2; 424/9.4, 93.1; 250/330, 334, 559.04, 559.05

(56) References Cited

U.S. PATENT DOCUMENTS

| | | | |
|---|---|---|---|
| 4,565,783 | 1/1986 | Hansen et al. | 435/305.1 |
| 4,637,053 | 1/1987 | Schalkowsky | 282/128 |
| 4,963,035 | 10/1990 | McCarthy et al. | 382/110 |
| 5,268,966 | 12/1993 | Kasdan | 382/133 |
| 5,403,722 | 4/1995 | Floeder et al. | 435/39 |
| 5,660,999 | 8/1997 | Naumann et al. | 435/34 |
| 5,733,693 | 3/1998 | Nohr et al. | 430/21 |

OTHER PUBLICATIONS

Shen et al. Application of Shape Analysis of Mammographic Calcifications, IEEE Transections on Medical Imaging, vol. 13, iss 2, p. 263–274, Jun. 1994.*

* cited by examiner

*Primary Examiner*—Jay Patel
(74) *Attorney, Agent, or Firm*—Bachman & LaPointe, P.C.

(57) ABSTRACT

A method for counting objects in an image includes the steps of: (a) providing an image including at least one object defined in the image in shades of at least one color; (b) identifying objects in the image having a shade of color which exceeds a threshold shade so as to provide a number of identified objects; (c) evaluating objects of the number of identified objects based upon object criteria to determine whether each object satisfies the criteria and can be counted, or does not satisfy the criteria and is suspect and needs further analysis; (d) repeating steps (b) and (c) for objects which are suspect at shades of color increasingly exceeding the threshold shade until all objects satisfy the criteria; and (e) providing a count of the objects, whereby accuracy of the count is enhanced. Each object is preferably tested for one or more criteria including object size, visibility, color, surface quality and shape.

23 Claims, 2 Drawing Sheets

SYSTEM FOR COUNTING COLONIES OF MICRO-ORGANISMS IN PETRI DISHES AND OTHER CULTURE MEDIA

This is a Continuation, of application Ser. No. 08/708,018, filed Aug. 30, 1996 now pending.

BACKGROUND OF THE INVENTION

The invention relates to a system and method for counting objects in a scanned image, and particularly to a system and method for counting colonies of micro-organisms in a culture media.

Detection and counting of micro-organisms is a universal problem in many diverse fields. Micro-organisms occur in almost all foods, in water, in air, and on numerous surfaces and substances with which humans come in contact. Such micro-organisms are often harmful and therefore must be measured and controlled.

A widely used practice for measuring the presence of micro-organisms is to place a sample of the substance to be tested, suitably prepared, on a nutrient surface such as agar, and to allow the micro-organism to grow into colonies. Standard dishes for use with such nutrient materials are called petri dishes, and a widely used commercial replacement for petri dishes is a film product provided by 3M under the trademark Petrifilm. When cultured in such a medium, colonies become visible to the eye and can be counted. Each visible colony corresponds to one original micro-organism.

An example wherein such a test occurs is in the dairy industry, where every shipment of milk from every farm must be tested for harmful bacteria. The accuracy of the count of colonies is of critical importance. Automatic counting machines have been available in the past, but their use is limited. One reason for this is that many unique problems arise that require the judgement of a human counter. Bacteria of different types produce colonies with diverse appearance that must be counted separately. Further, colonies may be small and light, large and dense, or clumped into large masses that overlap. Colonies may also have differing color or surface qualities, may produce gas bubbles, and may liquify the nutrient material thereby spreading over wide areas. Existing colony counter devices use binary (black and white) images wherein much of the detail information about objects is lost. Such devices are largely incapable of dealing with the afore-described problems in counting colonies.

There is therefore a need for a system and method for counting colonies that is capable of separating various objects that occur in a petri plate or other media so as to provide a more accurate count of colonies.

It is therefore the primary object of the present invention to provide a method for counting objects in an image wherein accuracy of the count is enhanced.

It is a further object of the present invention to provide a system for carrying out the method of the present invention.

It is still another object of the present invention to provide a system and method as above which corrects the count of objects or colonies based on one or more colony object characteristics such as: visibility, object color, object proximity, object vicinity, object shape, and object spreading.

Other objects and advantages of the present invention will appear hereinbelow.

SUMMARY OF THE INVENTION

In accordance with the present invention, the foregoing objects and advantages are readily attained.

According to the invention, a method is provided for counting objects in an image, which method comprises the steps of: (a) providing an image including at least one object defined in said image in shades of at least one color; (b) identifying objects in said image having a shade of color which exceeds a threshold shade so as to provide a number of identified objects; (c) evaluating objects of said number of identified objects based upon object criteria to determine whether each object satisfies said criteria and can be counted, or does not satisfy said criteria and is suspect and needs further analysis; (d) repeating steps (b) and (c) for objects which are suspect at shades of color increasingly exceeding said threshold shade until all objects satisfy said criteria; and (e) providing a count of said objects, whereby accuracy of said count is enhanced.

In further accordance with the invention, objects are filtered and may be rejected or not counted based upon object visibility, color, proximity, vicinity, shape and spreading so as to adjust the count of objects for these sources of inaccuracy.

BRIEF DESCRIPTION OF THE DRAWINGS

A detailed description of preferred embodiments of the invention follows, with reference to the attached drawings, wherein.

DETAILED DESCRIPTION

The invention relates to a system for counting objects in an image, especially a scanned or raster image, and particularly to a system for counting colonies of micro-organisms in a culture media such as a petri dish or Petrifilm™ film containing nutrient materials and a sample of the product, food or other material to be tested. Objects in other scanned environments or images could also be counted in accordance with the invention.

Figure 1:
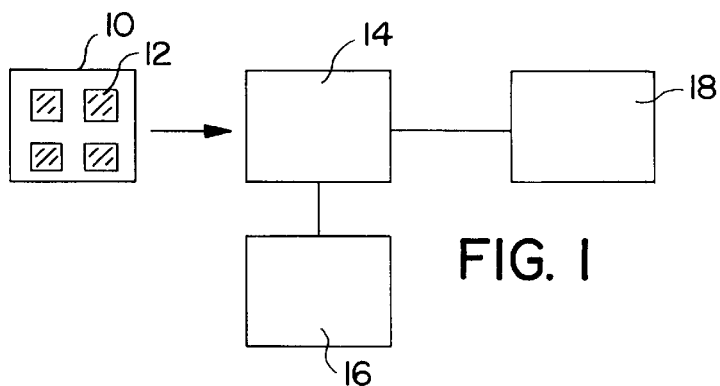
FIG. 1 is schematic illustration of a basic system in accordance with the present invention.

Referring to FIG. 1, an imaging device 10 is provided for creating a scanned, electronic or raster image of the petri plate or film 12 or other environment of interest. This scanned image is then transmitted to a computer or processor 14 by conventional means, and computer 14 is used or programmed to perform the method of the present invention and thereby obtain an accurate and reliable count of objects or colonies on the petri plate. Computer 14 may be controlled by conventional data entry means such as keyboard 16, and results may be output in printed form through printer 18, in visual form through a monitor (not shown) and in other well known manners.

In accordance with the invention, the imaging device can be a video camera using a two dimensional charge coupled detector (CCD) array. Alternatively, a one-dimensional camera containing a linear CCD array could be provided and used to generate a two dimensional image by moving the petri dish in steps perpendicular to the CCD array and taking multiple scans. The imaging device could also suitably be a table-top document scanner or other device commonly used in desk top publishing to enter documents and pictures into computers.

The computer or processor used to analyze the image may suitably be a conventional desk top personal computer or laptop such as an IBW™ or Macintosh™ or other compatible machine. Alternatively, an imbedded computer dedicated to the counting system can be provided, and for higher speeds, a work station may be provided such as those supplied by Hewlett Packard or Sun.

In accordance with the invention, a petri plate or dish to be analyzed or counted is scanned so as to provide the desired scanned image which, according to the invention, includes at least one object or colony defined in the image in varying shades of at least one color. Each image typically consists of one or three arrays of picture elements (pixels), with one array being provided for each color. The arrays are typically rectangular, usually square, and may have from several hundred to several thousand picture elements per side.

The scanning may be conducted so as to use color information if desired, or to use varying shades of a single color, for example, green. If the end counting requires color distinction, then typically three images are required. The following description of the present invention will be provided assuming that color is required. Of course, a monochrome version of the present method for counting clearly falls within the scope of the present invention.

In accordance with the invention, the image of interest is analyzed based upon the shades of color of objects defined in the image, and preferably also upon a number of additional criteria such as object visibility, color, proximity, vicinity, shape and spreading. Alternatively, a method is also provided in accordance with the invention whereby object shape is analyzed using Fourier series so as to determine whether a particular identified object is a single object or a number of objects merged together. These methods of the present invention are described below.

Starting with an electronic or scanned image of one or more petri dishes, the method of the present invention begins by analyzing a histogram of the image to identify a threshold shade as will be discussed below. In accordance with the invention, the histogram shows the relative frequency of each shade of color or gray for the image as a whole.

Objects or portions of objects are shown either as being darker than the threshold shade, or lighter than the threshold shade. Images having objects indicated in shades lighter than the threshold shade are similar to a "negative" image. For the purposes of the following disclosure, the method and apparatus of the present invention will be described as used with a "positive" image, or an image wherein objects are shown in shades darker than the threshold shade. Pixels having a shade of color darker than the threshold shade are deemed in accordance with the invention to represent an object or a portion of an object.

In accordance with the invention, the threshold shade is preferably selected so that objects or pixels having a shade darker than the threshold shade can with confidence be said to represent a colony or object which is to be counted. The threshold shade may suitably be selected from the histogram as follows. The histogram is provided as a frequency distribution of the various shades in the image as a whole. Typically, a large bell-shaped peak near the "white" end of the distribution results. This represents the background white in the image. Pixels corresponding to objects or colonies are darker and fewer in number, and are typically distributed over the lower end of the histogram. A small peak may be present near the dark end of the distribution indicating the relatively dark shade in the center of each colony.

The threshold shade or "basegray" is selected in accordance with the invention to be a shade value at or below the cusp of the bell-shaped peak representing the background white of the image. Pixels above this value are not considered to be object data, while pixels below this value are darker and are considered to belong to objects.

After determining basegray, or the threshold value, an initial count is made. This initial count, as well as the succeeding steps of an illustrative embodiment of the method of the present invention, are discussed below.

Initial Count

After determining basegray an initial count is made. The initial count may preferably be carried out as follows:

1. The image is run length encoded at the basegray value. This process expresses the image as a series of black runs each of which lies on a horizontal scan line and has a starting point and an ending point. At this point, the image is binary, that is, black and white.

2. The next step is to associate pixels of runs that are contiguous into groups. A run of pixels is contiguous with an adjacent run of pixels if they lie on adjacent lines and at least one pixel on the line above is directly over a pixel on the line below. These groups are numbered and constitute an initial list of objects.

3. Each object as defined above is then examined to determine if it should be counted as a separate object. Initial criteria for this testing preferably include object size, object shape, or a combination thereof. An object may be determined to be a separate object if it is small enough and if its extent in the X dimension and in the Y dimension are small enough. It may also be necessary to make further tests on the object such as determining the length of its periphery or whether the shape of the periphery is consistent with a single object. If the shape is round or oval, then we have a single object. If the shape is complex with concave sections or bumps, then it is not a single object. An object that passes the tests or filters is called "innocent" and can be counted. An object that does not pass the tests is called "suspicious" and is subject to further analysis.

Innocent objects are listed, along with their dimensions and characteristics in an output object list. Their runs are marked as being complete and not needing further analysis.

The remaining runs in the run list belong to suspicious objects that need to be further examined.

Suspicious objects are examined further according to the invention to see if a) they consist of more than one object or b) can be rejected.

Succeeding Counts

After the initial count, which was carried out at basegray, additional counts are carried out. Each count is carried out at a value of gray one step below the previous count, that is, at a darker value of gray or a value exceeding the basegray or threshold shade by increasing amounts. After each count, some of the counted objects may pass the tests for innocence. If so, they are listed in the output list and their runs are marked as being complete. In further accordance with the invention, and as will be further described below, it is also preferable to keep track of objects which were previously suspicious and which subsequently are counted as one or more objects. In this way, "parent" objects for various counted objects can be recorded for subsequent analysis to determine whether such counted objects should be combined.

This process is repeated until all objects satisfy the criteria and there are no more suspicious objects, at which point the output list of objects is complete.

The above process may be made clearer by considering an analogy consisting of islands in a sea. The altitude of the islands is analogous to density. Some islands are small and have low altitude. Others are mountainous and may be close together with multiple peaks. Each small separate island and each peak of the larger islands is analogous to a colony. The process of the present invention serves to count the peaks (i.e. colonies).

If a "contour map" of all the "islands" at an altitude of ten feet is provided, all small islands will be counted correctly. However, large islands will be counted as one and their peaks will not be separated.

By obtaining contours at successive steps in altitudes, for example, ten feet apart, then small islands are counted and the mountainous ones are examined, contour by contour, until all the peaks have been separately identified.

This counting process results in a list or count of objects large and small along with their measurements and their characteristics. Recorded are the X extent, Y extent, and peak density of each object. Also recorded is the "parent" of each object, namely the initial object of which it was a part.

Figure 2:
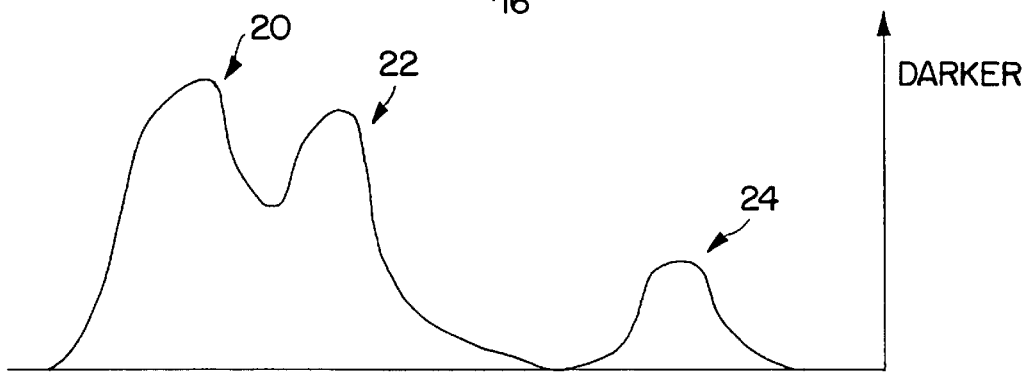
FIG. 2 is a graph illustrating the a density cross section for several colonies in a scanned image.
Figure 3:
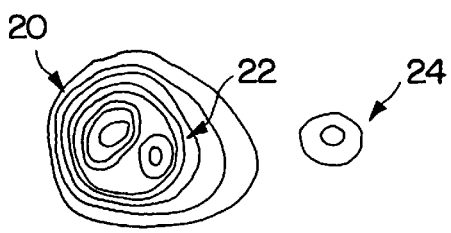
FIG. 3 is a contour drawing showing levels of darkness of the colonies represented in FIG. 1.
Figure 4:
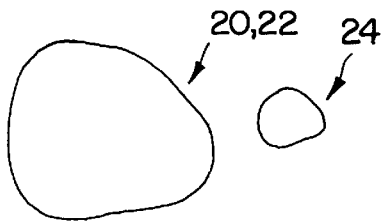
FIG. 4 illustrates objects counted at a relatively light threshold.
Figure 5:
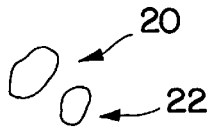
FIG. 5 illustrates objects scanned at a relatively dark threshold.
Figure 6:
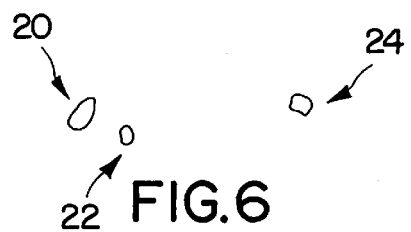
FIG. 6 illustrates the combination of objects counted at relatively light and darker thresholds in accordance with the present invention.

Referring now to FIGS. 2–6, the above process is further described. FIG. 2 shows a density cross section of three different objects, two of which 20, 22 are relatively dark and close together, and a third 24 which is relatively light and spaced from the other objects 20, 22. A contour map of shades or density of these objects is shown in FIG. 3. When evaluated at an initial threshold value of gray, object 24 is correctly counted, but objects 20, 22 are grouped together as a single large object as shown in FIG. 4. In accordance with the present invention, scanned objects 20, 22 as shown in FIG. 3 would be determined to be suspicious, for example based upon size, while object 24 would be accepted and added to a count. A further count would then be conducted at a darker shade of gray, in which count object 24 no longer appears, but objects 20 and 22 are now distinguishable as shown in FIG. 5. Objects 20, 22 are then accepted, and added to the count, and assuming no other objects are suspect, the count is complete. In accordance with this invention, the proper "peak" or objects 20, 22, 24 are properly counted as illustrated in FIG. 6. Further, a record is made that objects 20, 22 came from the same initial scanned object for subsequent testing to determine whether objects 20, 22 should be combined as "siblings" from the same parent.

The initial counting process results in a list of objects and their attributes, which may be stored as data in a data file in which each object is one data record. The remaining analysis consists mainly of analyzing the data, testing each object with one or more additional criteria or filter tests to characterize the data and determine whether certain objects should be included in the final count. Preferred filters, tests or criteria for use according to the invention are described below.

Visibility Filter

The first filter tests for visibility. The visibility filter serves to match the ability of the system to that of a human observer to see small objects. The unaided human eye is capable of seeing objects as small as about 1/40 mm in diameter but only if the contrast is high. The human ability to see small objects falls rapidly with contrast. On the other hand, a digital electronic imaging device is limited primarily by the number and spacing of separate and discrete sensing elements. For example, a video camera typically has about 700 by 500 such elements.

For the electronic camera or scanner, objects that are of sufficient contrast to be seen will be counted regardless of size. For this reason, given comparable resolution, the electronic device will "see" smaller objects than can be seen with the eye. The visibility filter compares the visibility value of each object and eliminates those that fall below a threshold value of a visibility index criteria.

The visibility of an object is a function of object size and contrast, typically the product of size and contrast. Size is preferably measured by the number of pixels in the object. Contrast is preferably the difference between the average background gray value and the darkest pixel in the object.

Objects whose visibility lie below the threshold value of visibility are deemed not sufficiently visible and are not counted. The limit can be varied to account for differences in acuity as desired for a particular application which may account for the human observer using a magnifying glass, and the like.

Colour Filter

Objects can also be distinguished and selected by color in accordance with the invention. For this purpose, the darkest point in each object is determined in each color image. A color is defined as a value of red, a value of green and a value of blue. Typically, each value ranges from 0 to 255 (dark to light), although numerous alternative designations may be used. As can be appreciated, these ranges yield over 16 million possible colors, however, very broad color ranges are sufficient.

For example, colonies are usually stained with a red dye. Other objects such as food particles and the like do not take up the stain and will be gray or black. In this case, it is sufficient to compare the red value with the green value. If the green value is less bright than the red value by a preset amount or threshold, the object is determined to be red and is counted.

Thus, according to the invention, at least two colors may preferably be present in the image, and one color may be an indication of an object of interest to be counted. Objects containing two or more colors may be tested according to the invention by comparing the relative darkness value or color content of each color in the object to a color threshold value to determine whether the object may be considered to be a color of interest.

Proximity Filter

Figure 7:
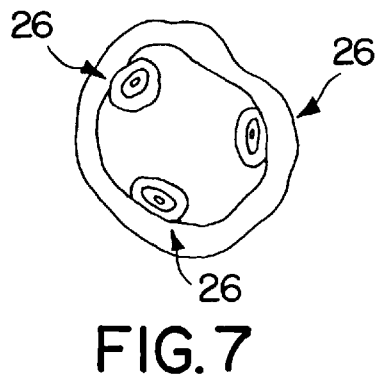
FIG. 7 illustrates a typical group of objects which may be counted as a single object after filtering with a vicinity filter in accordance with the present invention.

Referring to FIG. 7, an object may have a mottled surface that contains multiple dark areas 26. In this case, it could happen that each dark area 26 should not be counted as a separate object. The proximity filter process of the present invention is similar, on a smaller scale, to the process of separating colonies in a clump. On a large scale, the separate dark spots are individual colonies. On a small scale, they are variations in the surface of a single object.

The proximity filter determines whether a group of objects belong to a family that grew out of a single object, that is, they have a single parent object of which they are a part. Members of such a family (the siblings) are taken two at a time. If the distance between the pair of objects is less than a preset value, the smaller object of the pair is eliminated from the object list or count and its area is added to that of the larger object. By this process, only the largest of the siblings survives and is counted as desired.

In this filter, objects identified out of a larger parent suspect object are analyzed by comparing distance between pairs of such objects and combining pairs which are separated by a distance smaller than a preset threshold distance.

If the distance is greater than the preset amount both objects are deemed to be separate colonies and are counted.

Spreader Filter

In some cases, the micro-organism may partially dissolve the nutrient material. The colony then spreads over a large area, much larger than a typical colony. This type of object is called a "spreader". The edges of a spreader may be indistinct giving rise to a number of smaller objects. This entire set of objects arises from a single micro-organism and should be counted as a single object.

According to the invention, a filter to detect such an object first detects the original large object in the center as a spreader by size and shape. A very large light object, generally circular in shape, is a spreader.

An area in a band around the spreader is then analyzed, and any other object that may exist within this band is subjected to a visibility test as described above, but with stricter criteria requiring such an object to be larger and of higher contrast than the normal criteria in order to be counted as a colony. This eliminates the cloud of small objects typically occurring in the indistinct edge of a spreader, which should not be counted.

Vicinity Filter

Occasionally, in the immediate vicinity of large ordinary colonies, an effect similar to the edge effect of a spreader occurs. The edge may be somewhat indistinct, the background uniformity may be disturbed. In this case, a more severe visibility test in a band around the colony is used according to the invention to avoid counting extraneous objects that occur within this band in a similar manner to the test for a spreader discussed above. This is called a vicinity filter, and may suitably be incorporated into the filtering process for any object exceeding a preset or predetermined size.

Shape Filter

Colonies are usually round or almost round although the edge may be somewhat irregular. The X and Y dimensions of an object should be roughly equal and should be consistent with the area of the object. According to the invention, filters are provided for determining whether the shape of the object indicates two or more objects which have merged.

As indicated above, object size may be used as a filter for evaluating objects identified in an image of interest. In addition to size, a number of additional features of the shape of a particular object may be evaluated to enhance the accuracy of the count. Object width and object height, or preferably the ratio of width to height, may be evaluated to determine whether a multiple object is present.

A shape filter may also be used according to the invention to determine whether the edge of an object has indentations or the like which may be indicative of a multiple object.

Figure 8:
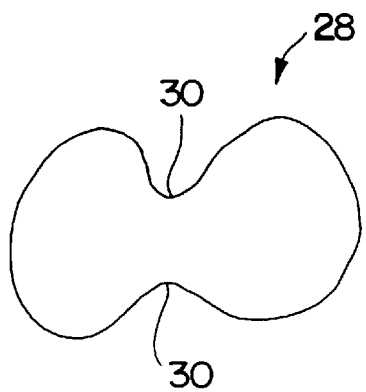
FIG. 8 illustrates the shape of an object which could be counted as two objects after filtering with a shape filter in accordance with the present invention.

Referring to FIG. 8, an object 28 that contains large concave indentations 30 may be a clump of several colonies instead of a single colony. For example, two colonies that partially overlap may have a dumbbell shape as shown.

According to the invention, geometric tests for such indentations may include measuring the precession of the tangent to the periphery of the object as one moves clockwise along the periphery. If the angle of the tangent changes continuously in one direction then the object has no indentations and has a shape indicative of a single object or colony. If the angle reverses direction one or more times then there are indentations that can be indicative of multiple colonies.

As set forth above, an alternative embodiment of the present invention includes the analysis of the edge or periphery of identified objects using Fourier series coefficients to determine whether a single object ar a complex object possibly including two or more objects is indicated. This procedure may suitably be incorporated into the various criteria discussed above, or may preferably be used in place of the shades of color testing of the above discussed embodiment of the method of the present invention.

In order to evaluate the periphery of an object using Fourier series coefficients, X,Y coordinates for each point around the edge of an object are assembled. A centroid or generally centrally located point is selected, and deviation from this point in the X and Y directions is plotted. This plot is then compared to a sine wave having varying frequencies corresponding to at least two harmonics. This provides information, preferably in the form of a number for the X and Y plots for each harmonic produced by multiplying the value of the harmonic with a corresponding value of the X or Y plot with which it is superimposed. This information, referred to as Fourier series coefficients, when considered together yield an excellent indication as to the shape of the object. For example, a sphere or generally elliptical object (single colony) is indicated by a relatively large number for the first harmonic and relatively small numbers for succeeding harmonics. Similarly, if the first and second harmonics produce relatively large numbers, a "dumbbell shape" (two colonies) such as that illustrated in FIG. 8 is indicated. A relatively small number for the first harmonic and a relatively large number for the second harmonic indicates a substantially "8" shaped object (also two colonies).

By analyzing the plots for additional harmonics, more and more detailed information regarding the exact shape of the periphery of an object can be obtained. However, for the purposes of the present invention, even a consideration of the first two or three harmonics yields quite useful information regarding the shape of the object without analyzing each point in the periphery in detail.

In most cases, all that is desired is the count of colonies. In these cases, it is sufficient to output the number of objects that have survived the filters in use for a particular process, which of course could include some or all of the above filters and others.

In other cases, it may be desirable to supply additional information about the colonies, not just their number. Such information may include size distribution, density distribution, and color distribution of the colonies, and may be provided in one or more tables. Such tables may readily be constructed from the object lists and their attributes.

Figure 9:
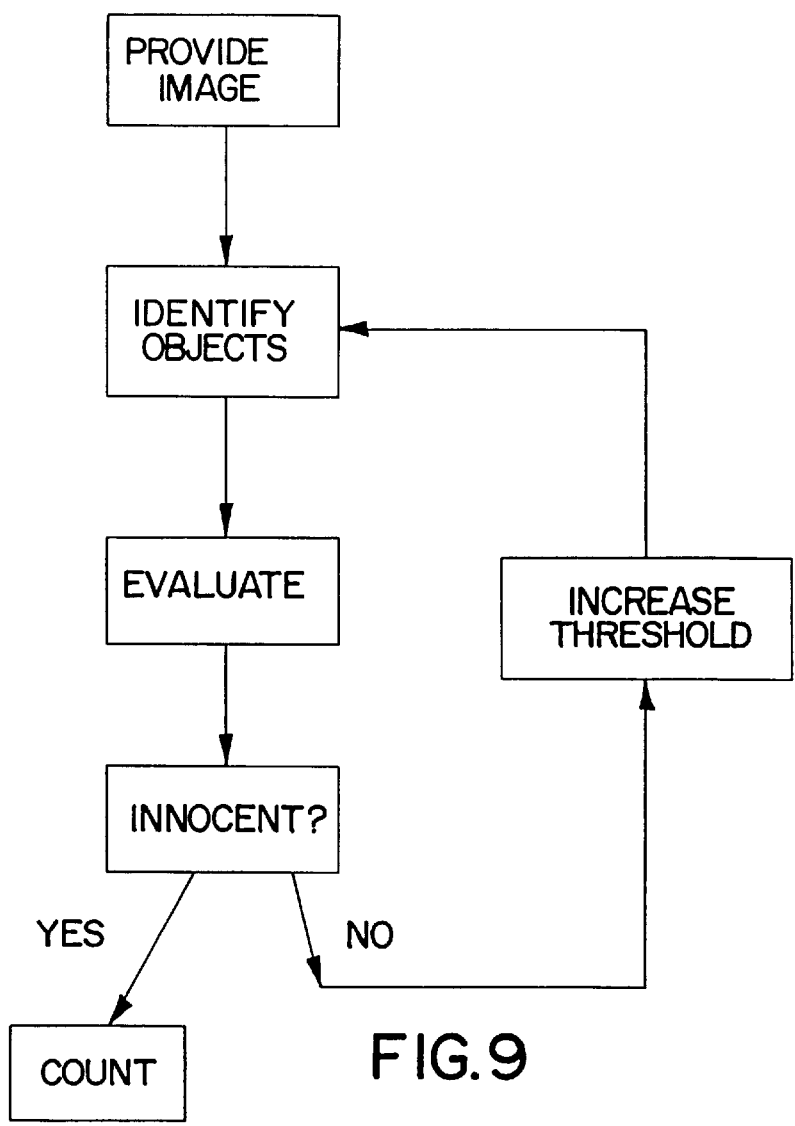
FIG. 9 is a flow chart illustrating the steps of a method for counting in accordance with the present invention.

Referring now to FIG. 9, a flow chart is provided which illustrate several steps in accordance with the method of the present invention. As set forth above, the method of the present invention preferably begins with the step of providing an image, preferably a scanned image, wherein objects are identified in varying shades of at least one color. As shown, the scanned image is analyzed according to with the invention so as to identify objects which have a shade exceeding the initial threshold shade. Each identified object is added to a list of objects, and this list of objects is evaluated to determine whether each individual object is expected to be a single object and is innocent, in which case the object is added to the overall count of objects, or whether the object is possibly more than one object, or not an object which should be counted, in which case the object is suspect and subjected to further evaluation at an increased threshold. When a cycle of evaluation is carried out and all objects deemed innocent, the evaluation process is complete and a final count can be provided.

In further accordance with the invention, the count as obtained above can be provided as the output of the method of the present invention or, alternatively, further evaluation or filtering can be conducted so as to further enhance the accuracy of the count provided by the method of the present invention. Additional filtering may be provided through the application of any or all of the additional tests identified above, as well as any further analysis which may be readily known to a person of ordinary skill in the art.

As set forth above, the method of the present invention may be used to advantageously provide enhanced accuracy of count of objects including colonies of micro-organisms in test samples so as to accurately provide an automated count of such objects. This advantageously allows for testing to be carried out in an automated manner while maintaining the accuracy of the counts obtained thereby. The method of the present invention advantageously serves to speed the measuring process without sacrificing accuracy, thereby rendering compliance with various requirements by industries such as the dairy industry far more attainable.

Although the above disclosure is presented in terms of measuring colonies of micro-organisms in test cultures such as food products, it should be readily apparent that the method for counting objects of the present invention could readily be used to count a wide variety of different types of objects in various different scannable environments, all within the scope of the present invention.

It is to be understood that the invention is not limited to the illustrations described and shown herein, which are deemed to be merely illustrative of the best modes of carrying out the invention, and which are susceptible of modifications of form, size, arrangement of parts and details of operation. The invention rather is intended to encompass all such modifications which are within its spirit and scope as defined by the claims.

What is claimed is:

1. A method for counting objects in an image, comprising the steps of:
   (a) providing an image including at least one object defined in said image in shades of at least one color;
   (b) identifying objects in said image having a shade of color exceeding a starting value of a threshold shade of color so as to provide identified objects;
   (c) determining a size of said identified objects;
   (d) comparing said size of said identified objects to a threshold size so as to provide a first group of objects having said size less than said threshold size, and a second group of suspect objects having said size greater than said threshold;
   (e) adding said first group of objects to a list of initially identified objects;
   (f) repeating steps (b)–(e) at incrementally increased values of said threshold shade until no objects are in said second group;
   (g) evaluating each object of said initially identified objects against object criteria to determine whether each object meets said criteria and can be counted, or does not meet said criteria and cannot be counted, wherein said object criteria comprises a visibility index, wherein said evaluating step comprises comparing object visibility of each object to said visibility index, wherein object visibility is defined as a function of object size and object contrast, and wherein said visibility index is a threshold value of said object visibility selected to adjust said list of initially identified objects for a given application; and
   (h) providing a final count of said initially identified objects which meet said criteria.

2. A method according to claim 1, wherein said threshold value of said object visibility is selected to emulate ability of an unimpaired human observer.

3. A method according to claim 1, further comprising the step of providing with said final count an indication as to which objects of said first group were initially in said second group.

4. A method according to claim 1, wherein said object criteria comprise said visibility index and at least one additional criteria selected from the group consisting of a color filter, a proximity filter, a spreader filter, a vicinity filter, and a shape filter.

5. A method according to claim 4, wherein said object criteria comprise said visibility index, said color filter, said proximity filter, said spreader filter, said vicinity filter, and said shape filter.

6. A system for counting objects in a given environment, comprising:
   means for providing an image of said environment including at least one object defined in said environment;
   analyzing means, associated with said means for providing, for:
   (1) identifying objects in said image having a shade of color exceeding a starting value of a threshold shade of color so as to provide identified objects;
   (2) determining a size of said identified objects;
   (3) comparing said size of said identified objects to a threshold size so as to provide a first group of objects having said size less than said threshold size, and a second group of suspect objects having said size greater than said threshold;
   (4) adding said first group of objects to a list of initially identified objects;
   (5) repeating steps (b)–(e) at incrementally increased values of said threshold shade until no objects are in said second group;
   (6) evaluating each object of said initially identified objects against object criteria to determine whether each object meets said criteria and can be counted, or does not meet said criteria and cannot be counted, wherein said object criteria comprises a visibility index, wherein said evaluating step comprises comparing object visibility of each object to said visibility index, wherein object visibility is defined as a function of object size and object contrast, and wherein said visibility index is a threshold value of said object visibility selected to adjust said list of initially identified objects for a given application; and output means for providing a final count of said initially identified objects which meet said criteria.

7. A method for counting objects in an image, comprising the steps of:
(a) providing an image including at least one object defined in said image in shades of at least one color;
(b) identifying objects in said image having a shade of color which exceeds a threshold shade so as to provide identified objects;
(c) evaluating said identified objects based upon object criteria to determine whether each object satisfies said criteria and can be counted, or does not satisfy said criteria and is suspect and needs further analysis, wherein said object criteria comprises a visibility index, wherein said evaluating step comprises comparing object visibility of each object to said visibility index, wherein object visibility is defined as a function of object size and object contrast, and wherein said visibility index is a threshold value of said object visibility selected to adjust counting of objects for a given application;
(d) repeating steps (b) and (c) for objects which are suspect at shades of color increasingly exceeding said threshold shade until all objects satisfy said criteria; and
(e) providing a count of said objects which satisfy said criteria, whereby accuracy of said count is enhanced.

8. A method according to claim 7, wherein said object criteria include an object size threshold, and wherein said evaluating step includes determining a size for each object and determining whether said size exceeds said size threshold.

9. A method according to claim 7, wherein said object criteria include a range of acceptable values of ratio of object width to object height, and wherein said evaluating step includes determining a width to height ratio for each object, and determining whether said width to height ratio is within said range.

10. A method according to claim 9, wherein said object criteria further include an object size threshold, and wherein said evaluating step further includes determining a size for each object and determining whether said size exceeds said size threshold.

11. A method according to claim 7, wherein said step of evaluating visibility comprises the steps of providing a threshold value of said visibility index, determining a visibility value for each object, and removing objects from said number of objects which have said visibility value less than said threshold value.

12. A method according to claim 7, wherein said step of providing said image comprises providing said image with objects defined in at least two colors, wherein objects to be counted are a different color than objects not to be counted, and wherein said object criteria include object color.

13. A method according to claim 7, wherein said image includes objects defined in at least two colors and said step of identifying said objects provides a number of said objects including a first color content and a second color content for said objects, and further comprising the steps of evaluating said objects based upon said first color content of said object indicating an object of interest and said second color content of said object indicating an object not of interest, and removing objects which have said second color content larger than a threshold value from said number of objects.

14. A method according to claim 7, further comprising the steps of identifying objects counted from a parent suspect object and respective distances between said objects, and evaluating distance between pairs of said objects counted from said parent suspect object based upon a threshold distance, and combining said pairs of objects when said distance is less than said threshold distance.

15. A method according to claim 7, wherein said step of identifying said objects provides a number of said objects including size and contrast of said objects and distance between said objects, and further comprising the steps of:
identifying an object exceeding a predetermined size;
selecting objects falling within a band of predetermined width at a predetermined distance from an object identified in said identifying step;
evaluating visibility of objects selected in said selecting step based upon said visibility index, and combining selected objects which do not meet said visibility index with said object identified in said identifying step.

16. A method according to claim 7, wherein said object criteria includes an object shape criteria, and said evaluating step includes determining shape characteristics of said objects and comparing said shape characteristics to said shape criteria.

17. A method according to claim 16, wherein said shape criteria include presence of indentations, number of indentations and relative size of indentations to said object.

18. A method according to claim 7, wherein said object criteria further include at least one additional criteria selected from the group consisting of object color, object proximity, object shape and combinations thereof.

19. A method according to claim 7, wherein said object criteria further comprise object color, object proximity and object shape.

20. A method according to claim 7, wherein said image is an image of a culture media and said objects are colonies of micro-organisms, and wherein said providing step provides a count of said colonies.

21. A method according to claim 7, wherein said step of providing said count includes providing size, density and color distribution of said objects.

22. A method according to claim 7, wherein said step (a) comprises the step of scanning an environment to provide a scanned image including said at least one object defined in said image in shades of at least one color.

23. A method according to claim 7, wherein said objects are darker in said image than said threshold shade, and wherein step (d) is carried out at shades of color increasingly darker than said threshold shade.

* * * * *